United States Patent
Wang

(10) Patent No.: US 10,202,648 B2
(45) Date of Patent: Feb. 12, 2019

(54) PROGNOSIS OF CHRONIC OBSTRUCTIVE PULMONARY DISEASE (COPD) AND TREAMENT FOR COPD

(71) Applicant: Jiu-Yao Wang, Tainan (TW)

(72) Inventor: Jiu-Yao Wang, Tainan (TW)

( * ) Notice: Subject to any disclaimer, the term of this patent is extended or adjusted under 35 U.S.C. 154(b) by 190 days.

(21) Appl. No.: 14/874,943

(22) Filed: Oct. 5, 2015

(65) Prior Publication Data

US 2016/0115537 A1   Apr. 28, 2016

Related U.S. Application Data

(60) Provisional application No. 62/059,383, filed on Oct. 3, 2014.

(51) Int. Cl.
  *C12Q 1/68* (2018.01)
  *C12Q 1/6883* (2018.01)
  *A61K 38/17* (2006.01)
  *G01N 33/68* (2006.01)

(52) U.S. Cl.
  CPC .......... *C12Q 1/6883* (2013.01); *A61K 38/395* (2013.01); *G01N 33/6884* (2013.01); *C12Q 2600/118* (2013.01); *C12Q 2600/156* (2013.01); *C12Q 2600/172* (2013.01); *G01N 2333/785* (2013.01); *G01N 2800/122* (2013.01)

(58) Field of Classification Search
  None
  See application file for complete search history.

(56) References Cited

PUBLICATIONS

Kim et al; Am J Respir Crit Care Med, vol. 186, pp. 1238-1247; Dec. 2012.*

* cited by examiner

*Primary Examiner* — Jehanne S Sitton
(74) *Attorney, Agent, or Firm* — Birch, Stewart, Kolasch & Birch, LLP

(57) ABSTRACT

The preset invention relates to a method for predicting the disease outcome and/or prognosis of chronic obstructive pulmonary disease (COPD) using a variant of surfactant protein D (SP-D) as a biomarker, which is the G-G-C-C-A haplotype of SP-D.

1 Claim, 4 Drawing Sheets

PROGNOSIS OF CHRONIC OBSTRUCTIVE PULMONARY DISEASE (COPD) AND TREAMENT FOR COPD

FIELD OF THE INVENTION

The present invention relates to a method for predicting the disease outcome and/or prognosis of chronic obstructive pulmonary disease (COPD) with a new biomarker, and a method for treating COPD. In particular, the present invention relates to a method for predicting the disease outcome of COPD using a variant of surfactant protein D (SP-D) as a biomarker, and a method for treating COPD using said SP-D.

BACKGROUND OF THE INVENTION

Chronic obstructive pulmonary disease (COPD), encompassing chronic bronchitis with or without emphysema, is currently the seventh leading cause of death in Taiwan and the third leading cause of death in the United States. Worldwide COPD morbidity and mortality are expected to increase dramatically in the next ten years. Although cigarette smoking is the primary risk factor for COPD, not all smokers are equally likely to develop COPD in their lifetimes. It is suggested that genetics also plays an important role in the development of COPD. (Sandford A J, Silverman E K. Chronic obstructive pulmonary disease (Susceptibility factors for COPD the genotype-environment interaction. *Thorax* 2002; 57: 736-741); and identifying genetic determinants and investigating their functions may lead to beneficial progress in understanding COPD pathobiology, diagnosis, and treatment (Sandford A J, Silverman E K. Chronic obstructive pulmonary disease. 1: Susceptibility factors for COPD the genotype-environment interaction. *Thorax* 2002; 57: 736-741).

Surfactant protein-D (SP-D), which lines the alveolar epithelium, is synthesized in type II pneumocytes and Clara cells as a large multimeric, calcium binding hydrophilic protein (Kishore U, Greenhough T J, Waters P, Shrive A K, Ghai R, Kamran M F, Bernal A L, Reid K B, Madan T, Chakraborty T. Surfactant proteins SP-A and SP-D: structure, function and receptors. *Mol Immunol* 2006; 43: 1293-1315). SP-D, as an innate immunity molecule, plays an important role in host defense and regulation of inflammation, which are essential factors in the pathogenesis of asthma (Wang J Y, Reid K B M. The immunoregulatory roles of pulmonary surfactant protein A and D in allergic inflammation of asthma. *Immunobiol* 2007; 212: 417-425), lung injury (Aono Y, Ledford J G, Mukherjee S, Ogawa H, Nishioka Y, Sone S, Beers M F, Noble P W, Wright J R. Surfactant protein-D regulates effector cell function and fibrotic lung remodeling in response to bleomycin injury. *Am J Respir Crit Care Med* 2012; 185: 525-536), and COPD (Hartl D, Griese M. Surfactant protein D in human lung diseases. *Eur J Clin Invest* 2006; 36: 423-435.). Several studies also found genetic variants of the SFTPD gene were associated with serum concentrations of SP-D.

SP-D is thought to play an significant role in the pathogenesis of COPD by reducing oxidant production (Groves A M, Gow A J, Massa C B, Laskin J D, Laskin D L. Prolonged injury and altered lung function after ozone inhalation in mice with chronic lung inflammation. *Am J Respir Cell Mol Biol* 2012; 47: 776-783), inflammatory responses in alveolar macrophages (Liu C F, Chen Y L, Chang W T, Shieh C C, Yu C K, Reid K B, Wang J Y. Mite allergen induces nitric oxide production in alveolar macrophages via the CD14/ TLR4 complex, and is inhibited by surfactant protein D. *Clin Exp Allergy* 2005; 35: 1615-1624), and increasing apoptotic cell clearance (Jäkel A, Clark H, Reid K B, Sim R B. The human lung surfactant proteins A (SP-A) and D (SP-D) interact with apoptotic target cells by different binding mechanisms. *Immunobiology* 2010; 215: 551-558). In known animal studies, increased oxidant production and reactive oxygen species are noted in the lungs of SP-D$^{-/-}$ mice (Yoshida M, Korfhagen T R, Whitsett J A. Surfactant protein D regulates NF-B and Matrix metalloproteinase production in alveolar macrophages via oxidant-sensitive pathways. *J Immunol* 2001; 166: 7514-7519). Furthermore, mice that lack SP-D develop chronic inflammation and emphysema that can be prevented by administration of truncated recombinant human SP-D (Knudsen L, Ochs M, Mackay R, Townsend P, Deb R, Muhlfeld C, Richter J, Gilbert F, Hawgood S, Reid K, Clark H. Truncated recombinant human SP-D attenuates emphysema and type II cell changes in SP-D deficient mice. *Respir Res* 2007; 8: 70-76). In fact, a higher level of serum SP-D is suggested as a biomarker associated with COPD risk (Celli B R, Locantore N, Yates J, Tal-Singer R, Miller B E, Bakke P, Calverley P, Coxson H, Crim C, Edwards L D, Lomas D A, Duvoix A, MacNee W, Rennard S, Silverman E, Vestbo J, Wouters E, Agusti A; ECLIPSE Investigators. Inflammatory biomarkers improve clinical prediction of mortality in chronic obstructive pulmonary disease. *Am J Respir Crit Care Med* 2012; 185: 1065-1072; Sin D D, Leung R, Gan W Q, Man S P. Circulating surfactant protein D as a potential lung-specific biomarker of health outcomes in COPD: a pilot study. *BMC Pulm Med* 2007; 7: 13). Foreman and colleagues demonstrated that certain genetic variants of SP-D are associated with changes in serum concentrations of SP-D and lung function, suggesting that SP-D is involved in the pathogenesis of COPD (Foreman M G, Kong X, DeMeo D L, Pillai S G, Hersh C P, Bakke P, Gulsvik A, Lomas D A, Litonjua A A, Shapiro S D, Tal-Singer R, Silverman E K. Polymorphisms in surfactant protein-D are associated with chronic obstructive pulmonary disease. *Am J Respir Cell Mol Biol* 2011; 44: 316-322). Genetic associations of SP-D with COPD were first investigated early in 2001 and focused mainly on a Mexican population (Guo X, Lin H M, Lin Z, Montario M, Sansores R, Wang G, DiAngelo S, Pardo A, Selman M, Floros J. Surfactant protein gene A, B, and D marker alleles in chronic obstructive pulmonary disease of a Mexican population. *Eur Respir J* 2001; 18: 482-490). Van Diemen et al showed that the rs2243639 (Thr160Ala) SFTPD SNP was associated with FEV$_1$/inspiratory vital capacity (Van Diemen C C, Postma D S, Aulchenko Y S, Snijders P J, Oostra B A, Van Duijn C M, Boezen H M. Novel strategy to identify genetic risk factors for COPD severity: a genetic isolate. *Eur Respir J* 2010; 35: 768-775). However, they did not encompass the whole block of the SFTPD gene and only picked up two loci, rs721917 (Met11Thr) and rs2243639 (Thr160Ala), as risk targets Kim et al from the genome-wide association analysis suggested SP-D as serum biomarker as well as a genetic susceptibility marker of COPD (Kim D K, Cho M H, Hersh C P, Lomas D A, Miller B E, Kong X, Bakke P, Gulsvik A, Agusti A, Wouters E, Celli B, Coxson H, Vestbo J, MacNee W, Yates J C, Rennard S, Litonjua A, Qiu W, Beaty T H, Crapo J D, Riley J H, Tal-Singer R, Silverman E K, ECLIPSE, ICGN and COPD Gene Investigators. Genome-wide association analysis of blood biomarkers in chronic obstructive pulmonary disease. *Am J Respir Crit Care Med* 2012; 186: 1238-1247). As mentioned above, although genetic association studies highly suggest that the SFTPD gene contributes to the development of COPD, little comprehensive work has been done regarding the relationship between polymorphisms of the SFTPD gene and COPD-related phenotypes and disease outcomes.

SUMMARY OF THE INVENTION

It is unexpectedly found that genetic variants of SP-D causing functional changes of SP-D are associated with the manifestation of COPD. In the present invention, the relationship between the disease outcome and prognosis of COPD and genetic polymorphisms of SP-D has been established.

Accordingly, in one aspect, the invention provides a method for predicting the disease outcome of COPD using genetic polymorphisms of SP-D.

In another aspect, the invention provides a method for predicting the prognosis of COPD using genetic polymorphisms of SP-D.

One embodiment of the invention is a method for predicting the disease outcome and/or prognosis of COPD using a genetic variant of SP-D.

In one example of the invention, the genetic variant of SP-D is the G-G-C-C-A haplotype of SP-D.

In further aspect, the invention provides a method for treating COPD comprising administering to a subject in need thereof a pharmaceutical composition comprising an effective amount of a genetic variant of SP-D that is the G-G-C-C-A haplotype of SP-D.

In other words, the invention provides a use of a genetic variant of SP-D that is the G-G-C-C-A haplotype of SP-D in the manufacturing a medicament for treating COPD, or a pharmaceutical composition for treating COPD comprising an effective amount of a genetic variant of SP-D that is the G-G-C-C-A haplotype of SP-D, and a pharmaceutically acceptable carrier.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

FIG. 1 shows that SP-D serum levels are associated with some disease outcomes of COPD; including:

DETAILED DESCRIPTION OF THE INVENTION

Figure 1A:
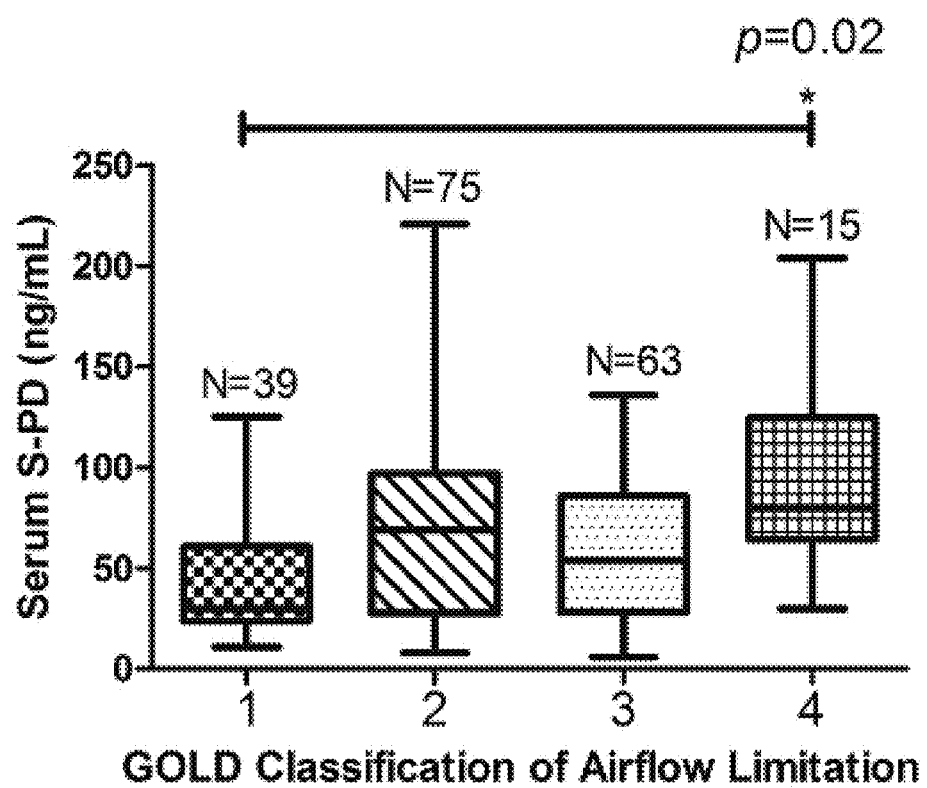
FIG. 1(A) shows the association between SP-D serum levels and the degree of airflow obstruction, as classified by GOLD guidelines (GOLD 4 vs. GOLD 1: p=0.02); wherein GOLD 1, 2, 3 and 4 represent FEV1≥80% of predicted, 50%≤FEV1<80% of predicted, 30%≤FEV1<50% of predicted, and FEV1<30% of the predicted value. FEV1: forced expiratory volume in the first second.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the abbreviation list is given below.

| | |
|---|---|
| COPD | chronic obstructive pulmonary disease |
| ELISA | enzyme-linked immunosorbent assay, |
| FEV1 | forced expiratory volume in the first second |
| GOLD | Global Initiative for Chronic Obstructive Lung Disease |
| IL | Interleukin |
| SP-D | surfactant protein-D |
| SNP | single nucleotide polymorphism |
| TNF-α | tumor necrosis factor-α |

As used herein, the term "chronic obstructive pulmonary disease (COPD)," also known as chronic obstructive lung disease (COLD), and chronic obstructive airway disease (COAD), refers to a type of obstructive lung disease characterized by chronically poor airflow. The main symptoms include shortness of breath, cough, and sputum production. Most people with chronic bronchitis have COPD. Tobacco smoking is the most common cause of COPD.

According to the invention, a method for predicting the disease outcome and/or prognosis of a pulmonary disease using a variant of SP-D. In one example, the variant of SP-D is the G-G-C-C-A haplotype of SP-D.

It is demonstrated in the examples that among 320 smokers (192 patients with COPD and 128 persons at-risk for COPD) who were prospectively monitored for at least three years; and the serum levels of SP-D in COPD patients were significantly associated with the degree of airflow obstruction and frequency of exacerbation. In the Haplotype association analysis, it is revealed that a variant of SP-D, i.e., the haplotype G-G-C-C-A, was associated with lower risk of COPD (p=0.03) in the study population. It is found that the COPD patients with the haplotype G-G-C-C-A had lower serum SP-D levels (p<0.001), higher rates of positive response to bronchodilator treatment (p=0.01), more improvement of $FEV_1$ in yearly follow-up (p=0.03), and better three-year survival rate than COPD patients with non G-G-C-C-A haplotype (p=0.03). It is concluded that this genetic haplotype of SP-D may serve as a valuable prognostic indicator of COPD.

Accordingly, the invention provides a method for predicting the disease outcome and/or prognosis of chronic obstructive pulmonary disease (COPD) using a variant of surfactant protein D (SP-D) as a biomarker, which is the G-G-C-C-A haplotype of SP-D.

In one example of the present invention, the method for predicting the disease outcome and/or prognosis of COPD comprises the steps of:

collecting a sample of a patient;

determining the presence or absence of the G-G-C-C-A of SP-D in the sample;

wherein the presence of the G-G-C-C-A haplotype in the sample means that the patient has a lower risk for mortality in COPD.

In the present invention, the sample may be any biologic samples from patients, such as bodily fluids, like a blood sample, a urine sample or a saliva sample.

In addition, the invention provides a method for treating COPD. The method comprises administering to a subject in need thereof a pharmaceutical composition comprising an effective amount of a genetic variant of SP-D that is the G-G-C-C-A haplotype of SP-D. In other words, the invention provides the use of a genetic variant of SP-D that is the G-G-C-C-A haplotype of SP-D in the manufacture of a medicament for treating COPD.

The invention also provides a pharmaceutical composition for treating COPD comprising an effective amount of a genetic variant of SP-D that is the G-G-C-C-A haplotype of SP-D, and a pharmaceutically acceptable carrier.

The term "subject" as used herein refers to an animal and a human, preferably a mammal, most preferably a human, who has been the object of treatment, observation or experiment. Furthermore, the terms "human," "patient" and "subject" are used interchangeably herein.

The term "effective amount" as used herein means that amount of composition that elicits the biological or medicinal response in a tissue, system, animal or human that is being sought by a researcher, dentist, veterinarian, medical doctor or other clinician. in one embodiment, the effective amount is a "therapeutically effective amount" for the alleviation of the symptoms of the disorder or condition being treated. In another embodiment, the effective amount is a "prophylactically effective amount" for prophylaxis of the symptoms of the disorder or condition being prevented.

The term "treating" or "treatment" of any condition or disorder refers, in one embodiment, to ameliorating the condition or disorder (i,e., arresting or reducing the development of the condition or at least one of the clinical symptoms thereof). In another embodiment "treating" or "treatment" refers to ameliorating at least one physical parameter, which may not be discernible by the subject. In yet another embodiment, "treating" or "treatment" refers to modulating the condition or disorder, either physically, (e.g., stabilization of a discernible symptom), physiologically, (e.g., stabilization of a physical parameter), or both. In yet another embodiment, "treating" or "treatment" refers to delaying the onset of the condition or disorder, or even preventing the same.

The term "pharmaceutical acceptable carrier" refers to one or more compatible solid or liquid filler diluents or encapsulating substances which are suitable for administration to an animal or a human, preferably mammal, most preferably a human. Typically, the carrier may be a solid, liquid, solution, suspension, gel, ointment, lotion, or combinations thereof.

In the invention, the composition or pharmaceutical composition may be formulated using any standard technology or commonly used methods known to those skilled in the art.

For use in therapy, therapeutically effective amounts of the protein, peptide, or functional variant thereof, may be formulated as a pharmaceutical composition for administration. Accordingly, the invention further provides a pharmaceutical composition comprising a therapeutically effective amount of a protein or peptide that is the G-G-C-C-A haplotype of SP-D, and a pharmaceutically acceptable carrier.

EXAMPLES

I. Methods

1. Populations for Experiments

The experimental group was defined as patients diagnosed with COPD, on the basis of their medical history, airway symptoms and signs, chest radiographic findings, and spirometric results, according to the diagnostic guidelines and criteria of the Global Initiative for Chronic Obstructive Lung Disease (GOLD). Chronic airway obstruction was defined as a ratio of post-bronchodilator forced expiratory volume in the first second ($FEV_1$)/forced vital capacity (FVC) less than 0.7 of predicted from pulmonary function testing, according to the current standard protocols of the American Thoracic Society (ATS) American Thoracic Society. Standardization of spirometry. *Eur Respir J* 2005; 26: 319-338). The control group consisted of healthy smokers with normal spirometry. All participants were prospectively monitored for at least three years, and all patients were in clinically stable condition and received appropriate COPD therapy recommended by GOLD guidelines[17]. The clinical stability was defined as neither exacerbated airway symptoms in need of antibiotics or corticosteroids, nor change of maintained inhalational drugs for a least 4 weeks prior to enrolment. The research protocol was approved by the ethics committee of National Cheng Kung University Hospital (BR-100-100), and the informed consent was obtained from each patient.

2. DNA Extraction and Genotyping

Genomic DNA was extracted from peripheral blood leukocytes using the QIAmp DNA Blood Midi Kit (Qiagen, Crawley, U K). We included two functional single nucleotide polymorphisms (SNPs) (rs2243639, Thr160Ala or 538A>G and rs721917, Met11Thr or 92T>C) with known functional effect on SFTPD gene expression[19] and then explored the tag SNPs on the HapMap Website (www.hapmap.org). A total of four tag SNPs for Han Chinese in Beijing (CHB) were selected to encompass the entire SFTPD gene using the Tagger-pairwise Tagging algorithm (filter: minor allele frequency (MAF)≥0.10 and $r^2$≥0.8). The SNPs were further genotyped using TaqMan chemistry as designed by Applied Biosystems (Foster City, Calif., USA). Haplotype block was then determined using the Haploview version 4.2 software (Daly lab at the Broad Institute, Cambridge, Mass., USA) and on the basis of the same genotyping data with a MAF≥0.10.

3. Serum SP-D Concentration and Measurement of Biomarkers

Serum SP-D concentrations were determined with an enzyme-linked immunosorbent assay (ELISA) kit (Biovendor, Inc., Heidelberg, Germany). Additionally, tumor necrosis factor (TNF)-α, interleukin (IL)-6, and IL-8 were also measured in plasma of subjects on enrolment using ELISA kits (R&D Systems, Inc., Minneapolis, Minn., USA).

4. Parameters for COPD-related Phenotypes

Post-bronchodilator $FEV_1$ was measured according to the ATS guidelines,[18] using equipment for lung function testing (Chestec 65, Chest Company, Tokyo, Japan). The severity of airflow obstruction was classified using $FEV_1$ according to the GOLD criteria.[17] The classification criteria were as follows: GOLD1=$FEV_1$/FVC<0.7 and $FEV_1$≥80% predicted; GOLD2=$FEV_1$/FVC<0.7 and 50%≥$FEV_1$<80% predicted; GOLD3=$FEV_1$/FVC<0.7 and 30%≥$FEV_1$<50% predicted; GOLD4=$FEV_1$/FVC<0.7 and $FEV_1$<30% predicted or $FEV_1$<50% predicted plus chronic respiratory failure. Post-bronchodilator spirometry was measured in the pulmonary function laboratory 20 minutes after the administration of inhaled fenoterol 400 μg. Additionally, patients were asked to eliminate short-acting bronchodilators for 8 hours and long-acting bronchodilators for 12-24 hours before testing. The frequency of a positive post-bronchodilator response, defined as the $FEV_1/FVC$ remains <0.7 with $FEV_1$>12% and >200 mL, was calculated. Pulmonary function test was measured annually for every patient. The changes of $FEV_1$ and frequency of medical visits were defined as the average of each in one year. Both hospitalization and emergency room visits for pulmonary symptoms and signs were regarded as medical visits due to exacerbated disease. We also categorized exacerbation risk as high, which was ≥2 medical visits per year in contrast to low, defined as <2 medical visits per year.

5. Outcome Evaluation

Survival status was obtained by research assistants who were blinded to the patients' baseline disease severity. After at least three years of follow-up, all patients' medical charts were reviewed, or patients were contacted by telephone about their survival status. Exact dates of death were obtained. All-cause mortality was registered.

6. Statistical Analysis

Data for continuous variables are presented as means±standard deviations (SDs) or number (%). For comparison of clinical information, the baseline differences between two independent groups (patients and controls, or patients with G-G-C-C-A/non G-G-C-C-A haplotype) were analyzed using the independent t-test and Chi-square test for comparison of continuous and nominal variables, respectively. Logistic regression modeling was used for further judgment of confounding factors, and odds ratios (OR) with 95% confidence intervals (CIs) were estimated. Kaplan-Meier survival analysis was used for outcome evaluations, which were compared with the log-rank test. Tests for comparison of significant alleles or genotypes between patients and controls were the Chi-square test or Fisher's exact test. We used the false discovery rate[20] to adjust for multiple testing. Hardy-Weinberg equilibrium analysis was calculated in accordance with standard procedures, also using the Chi-square test. Tests for haplotype association with susceptibility to COPD were performed using the Haploview Software 4.2. Statistically significant p values were corrected for multiple testing using permutation testing (1000 iterations randomly). A p value of <0.05 was considered significant. Statistical analyses were performed using SPSS Statistics 18 for Windows 7.

II. Results

1. Characteristics of COPD Patients and Healthy Smokers

From Jan 2003 to Jan 2010, there were 320 subjects consisting of 192 COPD patients and 128 healthy smokers who were enrolled in the study. The median duration of follow up was 35±22 months (range: 1 to 84 months). The baseline characteristics of the two groups are listed in Table 1A. Older age (68.6±11.4 years vs. 58.3±12.8 years, p<0.001), lower body mass index (BMI) (23.2±3.8 vs. 25.3±3.9, p<0.001), heavier smoking history (44.8±32.7 vs. 37.3±25.6 pack-years, p=0.02), and higher IL-8 level (4.4±6.0 vs. 2.2±2.5, p=0.002) were found in COPD patient group. Multivariate analysis using logistic regression modeling revealed that only age and smoking history were significant factors for susceptibility to COPD, see Table 1B.

TABLE 1A

Demographic characteristics of patients with chronic obstructive pulmonary disease (COPD) and healthy smoking controls.

| Univariate analysis | COPD (n = 192) | Control (n = 128) | p |
|---|---|---|---|
| Demographic parameters | | | |
| Age (yrs) | 68.6 ± 11.4 | 58.3 ± 12.8 | <0.001 |
| Male (%) | 100 | 100 | — |
| Body mass index | 23.2 ± 3.8 | 25.3 ± 3.9 | <0.001 |
| Smoking history (pack-yrs) | 44.8 ± 32.7 | 37.3 ± 25.6 | 0.02 |
| Current/Ex-smoker (%) | 23/77 | 20/80 | 0.56 |
| Spirometry | | | |
| $FEV_1/FVC$ | 53.3 ± 11.7 | 80.2 ± 6.3 | <0.001 |
| $FEV_1$ % of predicted | 57.9 ± 21.8 | 89.3 ± 5.2 | <0.001 |
| FVC % of predicted | 84.2 ± 18.5 | 97.5 ± 7.4 | 054 |
| Bronchodilator response (%) | 20 | 1 | <0.001 |
| Medical history | | | |
| Family history of COPD (%) | 34 | 30 | 0.41 |
| History of asthma (%) | 0 | 0 | — |
| Inflammatory cytokines, SP-D | | | |
| TNF-α (pg/mL) | 10.8 ± 9.0 | 9.4 ± 7.3 | 0.30 |
| IL-8 (pg/mL) | 4.4 ± 6.0 | 2.2 ± 2.5 | 0.002 |
| IL-6 (pg/mL) | 8.7 ± 26.5 | 4.1 ± 3.1 | 0.24 |
| SP-D (ng/mL) | 63.7 ± 43.8 | 69.3 ± 52.2 | 0.53 |

TABLE 1B

Multivariate regression analysis of the four significant parameters in the univariate analyses

| Multivariate analysis | COPD (n = 192) | Control (n = 128) | p |
|---|---|---|---|
| Demographic parameters | | | |
| Age (yrs) | 68.6 ± 11.4 | 58.3 ± 12.8 | <0.001 |
| Body mass index | 23.2 ± 3.8 | 25.3 ± 3.9 | 0.07 |
| Smoking history (pack-yrs) | 44.8 ± 32.7 | 37.3 ± 25.6 | 0.04 |
| Spirometry | | | |
| $FEV_1/FVC$ | 53.3 ± 11.7 | 80.2 ± 6.3 | <0.001 |
| $FEV_1$ % of predicted | 57.9 ± 21.8 | 89.3 ± 5.2 | <0.001 |
| Bronchodilator response (%) | 20 | 1 | <0.001 |
| Inflammatory cytokines, SP-D | | | |
| IL-8 (pg/mL) | 4.4 ± 6.0 | 2.2 ± 2.5 | 0.20 |

2. Association of SP-D Serum Level with COPD Severity

Figure 1B:
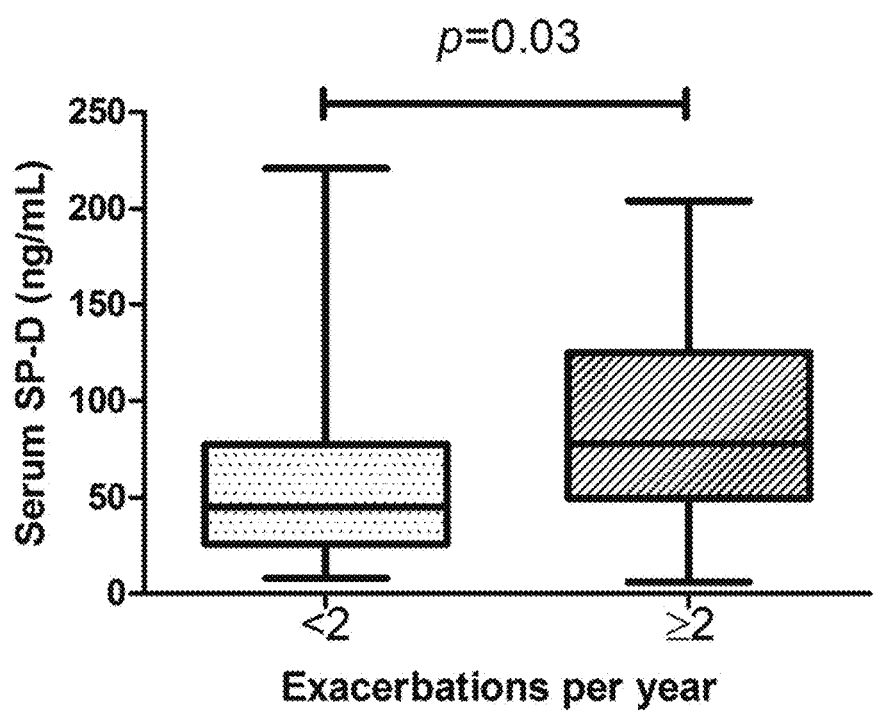
FIG. 1(B) shows the association between SP-D serum levels and exacerbation risk defined as the frequency of medical visits for COPD exacerbations per year (≥2 vs.<2 exacerbations per year, p=0.03).

Disease severity was assessed by degree of airflow obstruction (GOLD 1, 2, 3, or 4) and exacerbation risk (low or high). As illustrated in FIG. 1A, SP-D serum levels were significantly higher in the patient group with the most severe airflow obstruction (GOLD 4) compared to patients with the least severe obstruction (GOLD 1) (93.3±45.8 vs. 43.7±32.9 ng/ml, p=0.02). High risk of exacerbation (≥2 medical visits per year, 83.2±51.1 ng/ml SP-D) was significantly associated with higher SP-D serum levels than group with a low risk of exacerbation (<2 medical visits per year, 55.8±41.4 ng/ml SP-D) (p=0.03) (FIG. 1B).

3. Allele and Genotype Frequencies of SP-D

The information for each SNP of the SFTPD gene tested in our sample population is summarized in Table 2A, along with Hardy-Weinberg equilibrium data.

TABLE 2A

Summary of SNPs tested

| SNP ID | Gene symbol/ SNP type | Public location | MAF (from NCBI, CHB) | p for Hardy-Weinberg equilibrium Controls/ Patients |
|---|---|---|---|---|
| | Functional SNP | | | |
| rs2243639 | SFTPD/mis-sense | Chr. 10: 81691702 | 0.232 (G) | 0.92/0.80 |
| rs721917 | SFTPD/mis-sense | Chr. 10: 81696304 | 0.378 (C) | 0.26/0.39 |
| | Tag SNP | | | |
| rs911887 | LOC100288974; SFTPD/intron | Chr. 10: 81691503 | 0.423 (A) | 0.84/0.47 |
| rs10887199 | SFTPD/intron | Chr. 10: 81692814 | 0.345 (A) | 0.85/0.04 |
| rs2255601 | SFTPD/intron | Chr. 10: 81694539 | 0.352 (C) | 0.98/0.31 |
| rs726288 | SFTPD/intron | Chr. 10: 81696953 | 0.227 (G) | 0.81/0.49 |

Database was available on the web site of HapMap. Tests for Hardy-Weiberg equilibrium in patients and controls were represented as p value. MAF: minor allele frequency. CHB: Chinese Han in Beijing.

Database was available on the web site of HapMap. Tests for Hardy-Weiberg equilibrium in patients and controls were represented as p value. MAF: minor allele frequency. CHB: Chinese Han in Beijing.

Comparisons of allele and genotype frequencies between COPD and control groups are given in Table 2B and Table 2C. Before correction for the false discovery rate for multiple testing, dominant allele model of rs721917 increased the risk for COPD susceptibility (p=0.05, OR=1.2, 95% CI: 1.00-1.43). However, there was no statistical significance after correction for multiple testing.

TABLE 2B

Allele frequencies of SFTPD between patients and healthy smokers. MAF: minor allele frequency.

| SNP | Allele frequency COPD (N) | Control (N) | p |
|---|---|---|---|
| rs911887 | | | |
| G | 243 | 167 | 0.68 |
| A | 139 | 89 | |
| MAF | 0.364 | 0.348 | |
| rs2243639 | | | |
| A | 319 | 197 | 0.06 |
| G | 65 | 59 | |
| MAF | 0.169 | 0.230 | |
| rs10887199 | | | |
| G | 211 | 151 | 0.31 |
| A | 173 | 105 | |
| MAF | 0.451 | 0.410 | |
| rs2255601 | | | |
| T | 250 | 150 | 0.08 |
| C | 132 | 106 | |
| MAF | 0.346 | 0.414 | |
| rs721917 | | | |
| T | 253 | 148 | 0.05 |
| C | 131 | 106 | |
| MAF | 0.341 | 0.463 | |
| rs726288 | | | |
| A | 291 | 194 | 1 |
| G | 93 | 62 | |
| MAF | 0.242 | 0.242 | |

TABLE 2C

Genotype frequencies of SFTPD for patients with chronic obstructive pulmonary disease (COPD) and healthy smokers. The effect of dominant/recessive models of each SNP on the susceptibility to COPD was analyzed and corrected for the false discovery rate (FDR) of multiple testing

| SNP | | Genotype frequency COPD n (%) | Control n (%) | | p | OR (95% CI) | FDR |
|---|---|---|---|---|---|---|---|
| rs911887 | G/G | 75 (39.3%) | 55 (43.0%) | Dominant | 0.51 | 0.94 (0.78-1.13) | 0.64 |
| | A/G | 93 (48.7%) | 57 (44.5%) | | | | |
| | A/A | 23 (12.0%) | 16 (12.5%) | Recessive | 0.90 | 1.00 (0.57-1.89) | 0.82 |
| rs2243639 | A/A | 133 (69.3%) | 76 (59.4%) | Dominant | 0.07 | 1.32 (0.98-1.78) | 0.35 |
| | A/G | 53 (27.6%) | 45 (35.2%) | | | | |
| | G/G | 6 (3.1%) | 7 (5.5%) | Recessive | 0.30 | 0.98 (0.93-1.03) | 0.50 |
| rs10887199 | G/G | 65 (33.9%) | 44 (34.4%) | Dominant | 0.92 | 0.99 (0.84-1.17) | 0.77 |
| | A/G | 81 (42.2%) | 63 (49.2%) | | | | |
| | A/A | 46 (24.0%) | 21 (16.4%) | Recessive | 0.10 | 1.10 (0.98-1.23) | 0.25 |
| rs2255601 | T/T | 85 (44.5%) | 44 (34.4%) | Dominant | 0.07 | 1.18 (0.99-1.41) | 0.35 |
| | C/T | 80 (41.9%) | 62 (48.4%) | | | | |
| | C/C | 26 (13.6%) | 22 (17.2%) | Recessive | 0.38 | 0.96 (0.87-1.06) | 0.54 |
| rs721917 | T/T | 86 (44.8%) | 43 (33.9%) | Dominant | 0.05 | 1.20 (1.00-1.43) | 0.50 |
| | C/T | 81 (42.2%) | 62 (48.8%) | | | | |
| | C/C | 25 (13.0%) | 22 (17.3%) | Recessive | 0.29 | 0.95 (0.86-1.05) | 0.58 |
| rs726288 | A/A | 112 (58.3%) | 73 (57.0%) | Dominant | 0.82 | 1.03 (0.80-1.34) | 0.82 |
| | A/G | 67 (34.9%) | 48 (37.5%) | | | | |
| | G/G | 13 (6.8%) | 7 (5.5%) | Recessive | 0.64 | 1.01 (0.96-1.07) | 0.71 |

4. Haplotype Analysis of SP-D Between COPD Patients and Healthy Smokers

Figure 2:
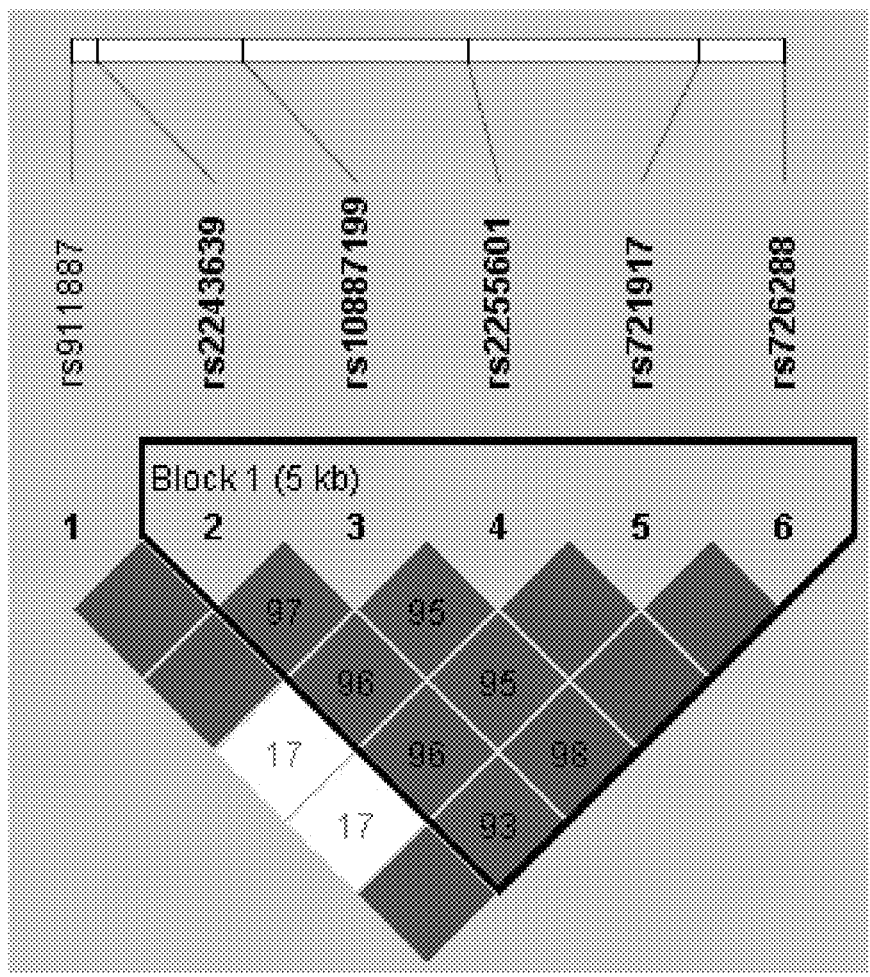
FIG. 2 shows the Haplotype block (delineated by bold lines) and tag SNPs of SP-D as determined with Haploview software, version 4.2; wherein the strength of the linkage disequilibrium (LD) between the two SNPs was measure by $r^2$ (r: correlation coefficient) (black: $r^2$=100 and is the strongest; white: $r^2$=0 is the weakest).

Haplotype analysis revealed that the frequency of the G-G-C-C-A haplotype was significantly higher in the control group compared with the COPD group (frequency in COPD group: 0.17 vs. 0.23 in the control group, p=0.03), suggesting that this haplotype played a potentially protective role in the development of COPD (FIG. 2 and Table 3).

TABLE 3

Haplotype analysis of SFTPD gene between patients and healthy smokers

| SNP markers | Haplotype | Frequency COPD (N = 192) | Control (N = 128) | p |
|---|---|---|---|---|
| rs2243639 | A-A-T-T-G | 0.24 | 0.24 | 0.91 |
| rs10887199 | A-G-T-T-A | 0.21 | 0.19 | 0.43 |
| rs2255601 | G-G-C-C-A | 0.17 | 0.23 | 0.03* |
| rs721917 | A-A-T-T-A | 0.20 | 0.16 | 0.16 |
| rs726288 | A-G-C-C-A | 0.17 | 0.17 | 0.85 |

*permutation p value.

5. Association of SP-D Haplotype with COPD-related Phenotypes

We analyzed the effect of SP-D G-G-C-C-A haplotype on COPD-related phenotypes, which included baseline demographic, pulmonary function, and systemic biomarkers. As listed in Table 4A, patients with haplotype G-G-C-C-A had better improvement of pulmonary function (p=0.03, OR=1.53) in the disease follow-up and were more sensitive to bronchodilator response (p=0.01, OR=1.72). The SP-D serum level was significantly lower in those patients with the G-G-C-C-A haplotype (p<0.001, OR=0.57).

TABLE 4A

Association of the G-G-C-C-A haplotype of SP-D with COPD-related phenotypes

| Haplotype analysis | G-G-C-C-A (n = 57) | non-G-G-C-C-A (n = 135) | Crude p | Adjusted p | OR (95% CI) |
|---|---|---|---|---|---|
| Demographic parameters | | | | | |
| Age (yrs) | 67.2 ± 12.5 | 69.1 ± 10.9 | 0.42 | — | — |
| Body mass index | 23.8 ± 3.6 | 23.0 ± 3.9 | 0.13 | — | — |
| Smoking history (pack-yrs) | 46.1 ± 35.0 | 44.3 ± 32.0 | 0.77 | — | — |
| Current smoker (%) | 19 | 21 | 0.57 | — | — |
| History of inhaled LAMA (%) | 32 | 35 | 0.45 | — | — |
| History of inhaled LABA + ICS (%) | 29 | 25 | 0.22 | — | — |
| History of inhaled LAMA + LABA + ICS (%) | 39 | 40 | 0.19 | — | — |
| Clinical parameters | | | | | |
| FEV1 % predicted | 56.4 ± 20.9 | 58.3 ± 22.7 | 0.59 | — | — |
| Medical visit (times/yr) | 1.0 ± 1.6 | 1.4 ± 2.4 | 0.36 | — | — |
| Change of FEV1 (mL/yr) | 128.6 ± 197.4 | 31.0 ± 161.8 | 0.01 | 0.03 | 1.53 (1.30-1.77) |
| Positive bronchodilator response (N/%) | 18/31.6 | 21/15.7 | 0.005 | 0.01 | 1.72 (1.49-1.91) |
| Inflammatory cytokines, SP-D | | | | | |
| TNF-α (pg/mL) | 10.2 ± 7.1 | 11.1 ± 9.6 | 0.92 | — | — |
| IL-8 (pg/mL) | 4.4 ± 6.2 | 4.3 ± 5.9 | 0.95 | — | — |
| IL-6 (pg/mL) | 6.7 ± 10.1 | 9.4 ± 30.5 | 0.57 | — | — |
| SP-D (ng/mL) | 52.6 ± 38.9 | 94.8 ± 42.2 | <0.001 | <0.001 | 0.57 (0.31-0.84) |

LAMA: long-acting muscarinic antagonist.
LABA: long-acting β2-agonist.
ICS: inhaled corticosteroid.
FEV1: forced expiratory volume in one second.
TNF-α: tumor necrosis factor-alpha.
IL-8: interleukin-8.
IL-6: interleukin-6.
SP-D: surfactant protein-D.

There were no other differences in demographic variables or inflammatory cytokines. In concordance with the results, we also found that the SP-D serum level positively correlated with the degree of airflow limitation and exacerbation risk in both groups of patients encompassing G-G-C-C-A and non G-G-C-C-A haplotypes, see Table 4B.

TABLE 4B

Correlation of SFTPD serum level with degree of airflow obstruction and exacerbation risk.

| Haplotype | GGCCA (N = 57) | | | non-GGCCA (N = 135) | | |
|---|---|---|---|---|---|---|
| | GOLD Classification of airflow obstruction | | | | | |
| | GOLD 1 | GOLD 4 | p | GOLD 1 | GOLD 4 | p |
| SFTPD (ng/mL) | 40.8 ± 33.7 | 86.1 ± 54.8 | 0.03 | 62.5 ± 32.6 | 106.3 ± 36.5 | 0.01 |
| | Exacerbation risk | | | | | |
| | <2 per year | ≥2 per year | p | <2 per year | ≥2 per year | p |
| SFTPD (ng/mL) | 42.0 ± 27.7 | 78.6 ± 52.9 | 0.01 | 83.8 ± 29.8 | 111.3 ± 31.5 | 0.02 |

In boldface if <0.05.

6. Effect of SP-D Haplotype on COPD Survival

Figure 3:
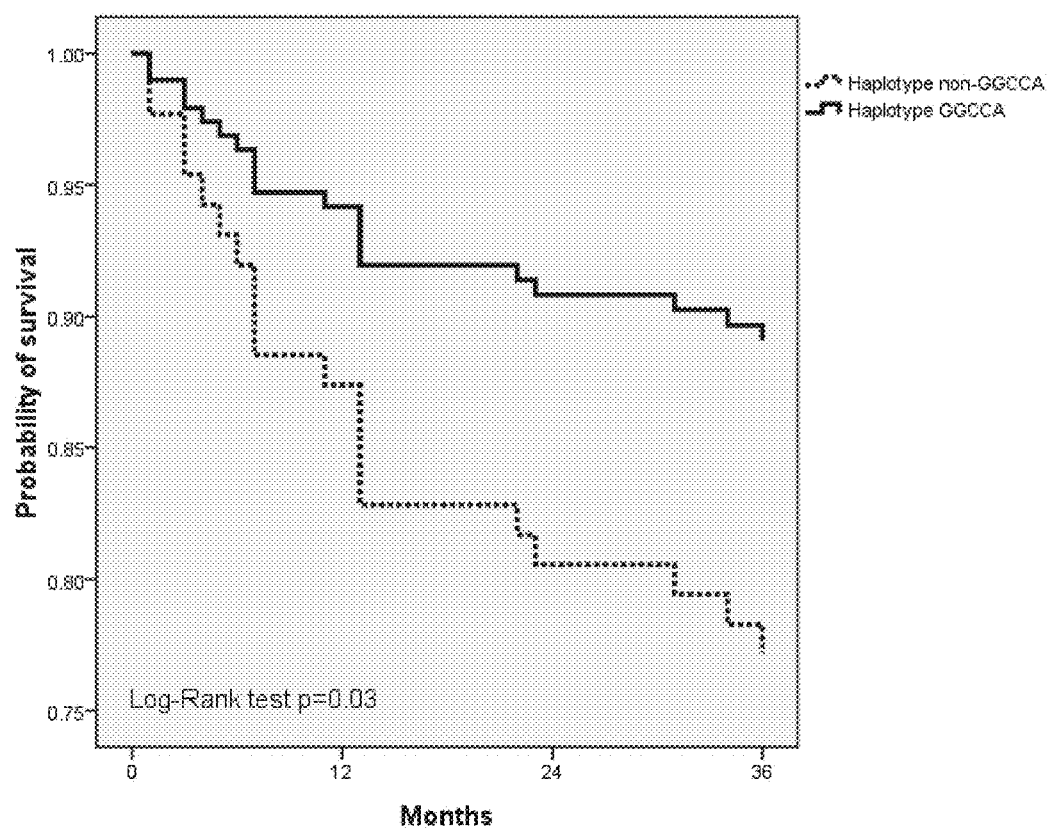
FIG. 3 shows the results of Kaplan-Meier survival analysis of patients with the G-G-C-C-A vs. non G-G-C-C-A haplotype.

FIG. 3 shows the significant difference in the 3-year survival between COPD patients with and without the G-G-C-C-A haplotype. The 3-year survival rate for patients with the haplotype G-G-C-C-A was 90%, while the rate among patients with the non-G-G-C-C-A haplotype was only 77% (p=0.03, log-rank test). Cox proportional hazard regression modeling (Table 5) revealed that worse airflow obstruction (HR: 0.92, 95% CI: 0.85-0.97), higher exacerbation risk (HR: 5.35, 95% CI: 2.34-8.44), and protective haplotype G-G-C-C-A (HR: 0.79, 95% CI: 0.33-0.89) were independently associated with the prognosis after adjustment for all the other confounding factors.

TABLE 5

Cox proportional hazard regression analysis for three-year mortality rate between patients with haplotype G-G-C-C-A/non G-G-C-C-A.

| Survival analysis | Crude p | Adjusted p | HR (95% CI) |
|---|---|---|---|
| Demographic parameters | | | |
| Age | 0.10 | — | — |
| Body mass index | 0.38 | — | — |
| Smoking history (pack-yrs) | 0.18 | — | — |
| Clinical parameters | | | |
| FEV1 % of predicted | 0.01 | 0.02 | 0.92 (0.85-0.97) |
| Medical visit (times/yr) | 0.02 | 0.03 | 5.35 (2.34-8.44) |
| Change of FEV1 (mL/yr) | 0.08 | | |
| Positive bronchodilator response (N/%) | 0.10 | | |
| SFTPD level and haplotype | | | |
| Haplotype G-G-C-C-A | 0.02 | 0.03 | 0.79 (0.33-0.89) |
| SFTPD (ng/mL) | 0.31 | | |

Given the above, it was found that there is a potential trend in the risk for dominant rs721917 model (p=0.05 before false discovery rate correction) toward COPD susceptibility. Further analyzing the entire SFTPD gene with four additional tag SNPs of SFTPD. It was demonstrated that a protective G-G-C-C-A haplotype (rs2243639, rs10887199, rs2255601, rs721917 and rs726288) is associated with the development of COPD; and the genetic influence on COPD susceptibility in a Chinese population in Taiwan. Therefore, it can be concluded that SP-D is involved in the predisposition to COPD.

It was further illustrated in these examples that the G-G-C-C-A haplotype of SP-D was not only associated with lower risk of COPD, but also COPD patients with the G-G-C-C-A haplotype had lower SP-D serum levels, higher rates of positive response to bronchodilator therapy, and better improvement of $FEV_1$ in yearly follow-ups. More importantly, as shown in a comparison in survival between subgroups of COPD patients for all-cause three-year mortality, there was a significant difference between COPD patients with and without the G-G-C-C-A haplotype. In our study population, the risk for three-year mortality in patients with the G-G-C-C-A haplotype was 21% lower than in patients with the non-G-G-C-C-A haplotype. There were 11 patients died within one year after enrolment, and the effect of G-G-C-C-A haplotype on survival among patients completing at 12 months follow-up period remained significant (data not shown).

In conclusion, serum levels of SP-D positively correlated with pulmonary function impairment at baseline and frequency of disease exacerbation in the follow up period. From subgroup analysis, the protective G-G-C-C-A haplotype of the SFTPD gene was an important biomarker for predictive and therapeutic modalities of COPD.

The descriptions and claims as provided should be understood as of demonstrative purpose instead of limitative in any way to the scope of the present invention.

I claim:

1. A method for detecting G-G-C-C-A haplotype in a sample of a patient comprising the steps of:
   collecting a sample of said patient;
   performing a genotyping assay and detecting the alleles at SNP ID rs2243639, SNP ID rs10887199, SNP ID rs2255601, SNP ID rs721917, and SNP ID rs726288 of surfactant protein D (SP-D) in the sample; and
   detecting the presence of the G-G-C-C-A haplotype of SP-D in the sample.

* * * * *